(12) United States Patent
Chen et al.

(10) Patent No.: US 6,439,889 B1
(45) Date of Patent: Aug. 27, 2002

(54) TEETH CREVICE CLEANING APPARATUS AND METHOD OF USING THE SAME

(76) Inventors: Shuqi Chen, 96 Naples Rd., Unit 2, Brookline, MA (US) 02446; Lingiun Chen, 96 Naples Rd., Unit 2, Brookline, MA (US) 02446

( * ) Notice: Subject to any disclaimer, the term of this patent is extended or adjusted under 35 U.S.C. 154(b) by 0 days.

(21) Appl. No.: 09/744,138

(22) PCT Filed: Jul. 23, 1999

(86) PCT No.: PCT/US99/16256

§ 371 (c)(1), (2), (4) Date: Jan. 19, 2001

(87) PCT Pub. No.: WO00/06045

PCT Pub. Date: Feb. 10, 2000

Related U.S. Application Data

(60) Provisional application No. 60/094,316, filed on Jul. 27, 1998.

(51) Int. Cl.[7] ............................................... A61C 15/00
(52) U.S. Cl. ....................................................... 433/216
(58) Field of Search ....................... 433/216, 93, 168.1, 433/214, 6, 71

(56) References Cited

U.S. PATENT DOCUMENTS

| | | | | | |
|---|---|---|---|---|---|
| 2,957,476 A | * | 10/1960 | Freeman | ..................... | 433/216 |
| 3,686,761 A | * | 8/1972 | Gravon | ..................... | 433/216 |
| 3,742,942 A | * | 7/1973 | Westline | ..................... | 433/216 |
| 4,059,101 A | * | 11/1977 | Richmond | ..................... | 433/216 |
| 4,164,940 A | * | 8/1979 | Quinby | ..................... | 433/216 |
| 4,624,640 A | * | 11/1986 | Tesini | ..................... | 433/71 |
| 5,104,315 A | * | 4/1992 | McKinley | ..................... | 433/216 |
| 5,235,991 A | * | 8/1993 | Minneman | ..................... | 433/71 |
| 5,346,395 A | * | 9/1994 | Adell | ..................... | 433/71 |
| 5,455,285 A | * | 10/1995 | Carroll | | |
| 5,503,552 A | * | 4/1996 | Diesso | ..................... | 433/71 |
| 5,800,167 A | * | 9/1998 | Adell | ..................... | 433/71 |

* cited by examiner

*Primary Examiner*—Todd E. Manahan
(74) *Attorney, Agent, or Firm*—Foley Hoag LLP

(57) ABSTRACT

A mouth pad for cleaning teeth crevices has a U-shaped plate sized to cover substantially only the biting surfaces of the upper and lower teeth of the human jaw. The plate is positioned between the upper teeth and lower teeth such that when the teeth are rinsed with a liquid, the liquid flows primarily through the crevices between individual teeth, and physically detaches the adhering residue within. A method of cleaning teeth using a plate positioned between the upper and lower teeth is also disclosed.

4 Claims, 3 Drawing Sheets

TEETH CREVICE CLEANING APPARATUS AND METHOD OF USING THE SAME

This application claims priority from Provisional application Ser. No. 60/094,316, filed Jul. 27, 1998.

INTRODUCTION

The present invention is directed to a teeth cleaning apparatus and, more particularly to a teeth cleaning apparatus which can efficiently clean crevices between the teeth.

BACKGROUND

Conventional dental cleaning methods have many limitations and disadvantages. Brushing the teeth can only clean the tooth surfaces that a brush can reach. Therefore, brushing cleans only the exposed surfaces of teeth, not the crevices between teeth. Flossing can reach most of these crevices, but it is inconvenient to use, particularly for children. Since plaque formation occurs after meals and its adhesion to teeth is enhanced with time, the plaque is much more easily removed immediately after meals. Because of the inconveniences of flossing, people rarely floss after each meal. As time goes by, the plaque becomes hard to remove. Rinsing teeth with mouthwash is convenient enough to be done immediately after meals. However, rinsing does not clean the crevices between teeth very well. When the jaw is closed, open spaces are typically formed between the upper and lower teeth. These spaces are much larger than the crevices between adjacent teeth. The larger spaces provide a shortcut for the mouthwash to bypass the crevices. Thus, when rinsing, most of the mouthwash or water flows through the larger open spaces between the upper teeth and the lower teeth, and only a very small amount of mouthwash may flow through the crevices. Not only is the amount of mouthwash flowing through the crevices reduced, the pressure applied on the crevices is also diminished due to the bypass of mouthwash through the open spaces, resulting in a lower flow rate in the crevices. Such a low flow rate of a small amount of mouthwash has insufficient wash power to clean the narrow crevices between the teeth. Hence, even if the mouthwash can kill bacteria, rinsing with mouthwash can hardly wash out the attached dead bacteria, plaque and other adhering residues on the tooth surfaces in the crevices. These remaining residues still provide bacterium with a breeding ground. Therefore, rinsing with mouthwash cannot effectively clean the narrow crevices between teeth. These narrow crevices are inhabited by plaque and other bacteria, which cause bad breath, tooth decay and cavities. Currently, there is no efficient and convenient way to clean them.

It is an object of the present invention to provide a teeth crevice cleaning apparatus which reduces or overcomes some or all of the aforesaid difficulties inherent in prior known devices. Particular objects and advantages of the invention will be apparent to those skilled in the art, that is, those who are knowledgeable or experienced in this field of technology, in view of the following disclosure of the invention and detailed description of certain preferred embodiments.

SUMMARY

The principle of the invention combines the convenience of rinsing with the function of flossing to create an easy-to-use, convenient and efficient dental care product. An apparatus is used to block the spaces between the upper teeth and the lower teeth during occlusion, that is, when the biting surfaces of the upper teeth and the lower teeth are brought together. In use, the apparatus does not cover or block the crevices between the teeth. Thus, when rinsing, the mouthwash is forced to flow through the crevices between the teeth rather than the spaces between the upper teeth and the lower teeth. This generates a high shear force, or wash power, that is applied on the tooth surfaces and washes away the residues in the crevices to prevent plaque from forming.

In accordance with a first aspect, an apparatus for cleaning teeth crevices has a U-shaped plate sized to cover substantially only the biting surfaces of upper and lower teeth of a human jaw.

In accordance with another aspect, a kit for cleaning teeth crevices comprises a U-shaped plate sized to cover substantially only the biting surfaces of upper and lower teeth of a human jaw and a liquid mouthwash.

In accordance with yet another aspect, a method of cleaning teeth includes the following steps: inserting a U-shaped plate sized to cover substantially only the biting surfaces of upper and lower teeth of a human jaw into a mouth of a user; drawing an appropriate amount of liquid into the mouth; biting down on the plate; rinsing the liquid repeatedly while biting down on the plate; spitting out the liquid; and removing the plate from the mouth.

From the foregoing disclosure, it will be readily apparent to those skilled in the art that the present invention provides a significant technological advance. Preferred embodiments of the present invention can provide increased efficiency, convenience and comfort in cleaning the crevices between adjacent teeth. These and additional features and advantages of the invention disclosed here will be further understood from the following detailed disclosure of certain preferred embodiments.

BRIEF DESCRIPTION OF THE DRAWINGS

Certain preferred embodiments are described in detail below with reference to the appended drawings wherein.

Figure 1:
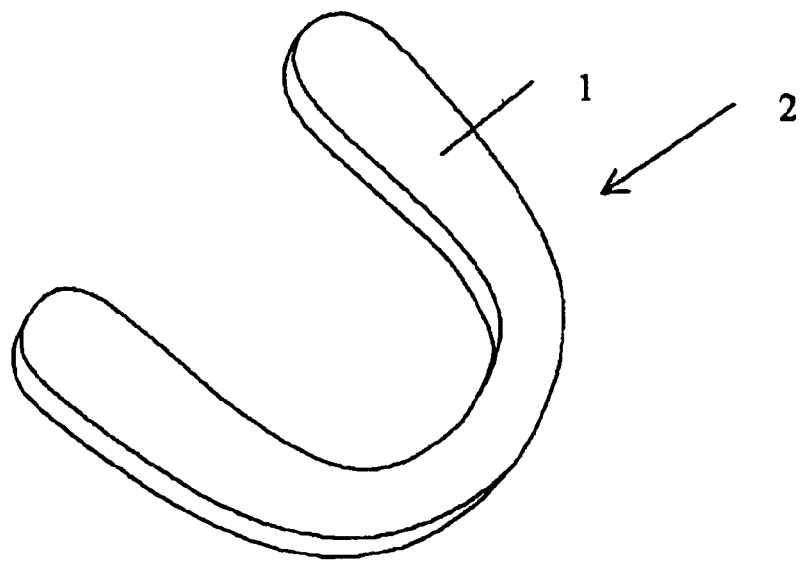
FIG. 1 is a schematic perspective view of a preferred embodiment of the teeth crevice cleaning apparatus of the present invention.

The figures referenced above are not drawn necessarily to scale and should be understood to present a representation of the invention, illustrative of the principles involved. Some features of the teeth crevice cleaning apparatus depicted in the drawings have been enlarged or distorted relative to others to facilitate explanation and understanding. The same reference numbers are used in the drawings for similar or identical components and features shown in various alternative embodiments. Teeth crevice cleaning apparatus as disclosed herein, will have configurations and components determined, in part, by the intended application and environment in which they are used.

DETAILED DESCRIPTION OF CERTAIN PREFERRED EMBODIMENTS

Referring to FIG. 1, a mouthpad according to the present invention is shown generally by the reference numeral 2.

Mouthpad, as used herein, refers to a device or apparatus which is inserted into the mouth of a user and is positioned between the user's upper and lower teeth to aid in cleaning crevices between adjacent teeth. Mouthpad 2 comprises a plate 1 having a U-shape. In certain preferred embodiments, plate 1 is made of a resilient, foam-like material, such as a polymer or other suitable materials. The U-shape of mouthpad 2 substantially matches a human jaw to cover substantially only the interfaces of all the teeth during occlusion, that is, when the biting surfaces of the upper and lower teeth are brought together. Thus, mouthpad 2 covers substantially only the biting surfaces of the teeth, leaving the crevices between adjacent teeth on the front and back of the teeth substantially unobstructed. Mouthpad 2 is sized to fit in between the upper teeth and the lower teeth during occlusion, and is preferably approximately 2 mm to 12 mm thick, most preferably approximately 5 mm to 8 mm thick. Thus, mouthpad 2 provides the function of blocking the spaces between the upper teeth and the lower teeth during occlusion. When rinsing with mouthpad 2, mouthwash or other liquid held in the mouth is advantageously forced to flow through the crevices between individual teeth rather than through the spaces between the upper teeth and the lower teeth. This generates a great shear force that is applied on the tooth surfaces and washes away any residue in the crevices to prevent plaque from forming. In certain preferred embodiments, mouthpad 2 can be disposable, while in other embodiments, mouthpad 2 may be reused.

Figure 2:
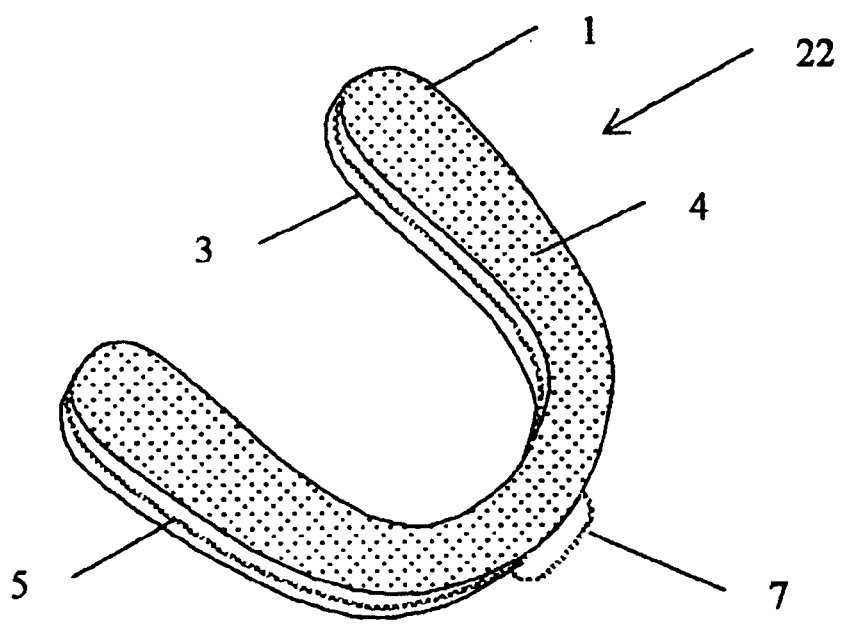
FIG. 2 is a schematic perspective view of an alternative embodiment of the teeth crevice cleaning apparatus of the present invention.

Another preferred embodiment is shown in FIG. 2. In this embodiment, plate 1 of mouthpad 22 has a sandwich structure formed of a top layer 4, a bottom layer 3, and a central layer 5 disposed between top and bottom layers 4, 3. Top and bottom layers 4, 3 are preferably made of a resilient, foam-like material, such as a polymer or other suitable material. Top and bottom layers 4, 3 are preferably approximately 2 mm to 6 mm thick and are attached respectively on each side of the central layer 5 by gluing, molding or other suitable means. Central layer 5 is a thin sheet of material capable of being easily shaped. Central layer 5 may be formed of a suitable malleable or ductile material, such as copper or cellulose, with a thickness of approximately 0.05 to 1 mm, depending on the material used. Central layer 5 functions as the skeleton of mouthpad 22. When a user bites down on mouthpad 22 for the first time, their teeth mold central layer 5 so that mouthpad 22 matches the profile of a user's teeth.

In certain preferred embodiments, as illustrated in FIG. 2, a handle 7 can be attached to mouthpad 22 in order to facilitate insertion and removal from the mouth. Handle 7 can be formed of any suitable material including, for example, plastic or foam.

Figure 3:
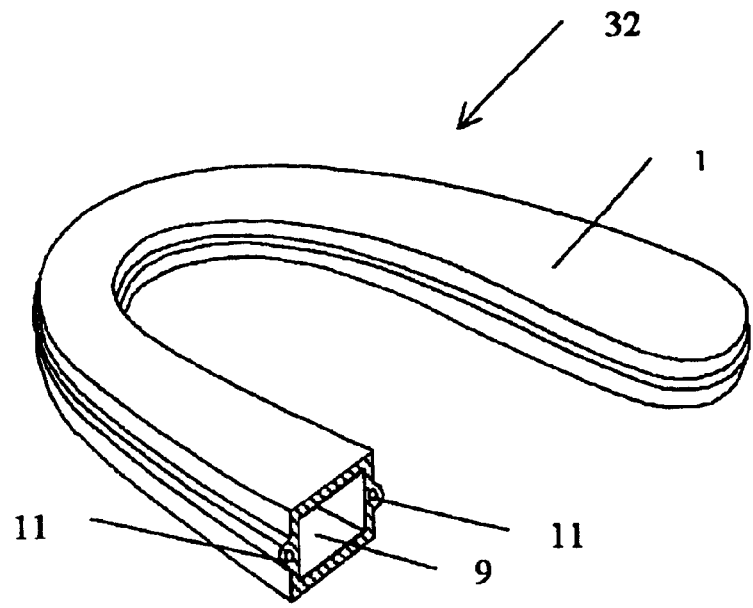
FIG. 3 is a schematic perspective view, shown partially in section, of another alternative embodiment of the teeth crevice cleaning apparatus of the present invention.

Another preferred embodiment is shown in FIG. 3, where mouthpad 32 contains a pocket 9. Pocket 9 typically contains air at ambient pressure, but may, in other preferred embodiments, contain other gases or fluids at any desired pressure. Mouthpad 32 is preferably formed of a resilient rubber-like material, such as, for example, polyvinyl chloride (PVC), nylon, or silicon rubber. Other suitable materials for mouthpad 32 will become readily apparent to those skilled in the art, given the benefit of this disclosure. In certain preferred embodiments, a stiffening member 11 is secured within mouthpad 32 adjacent its outer periphery. Stiffening member 11 serves as the skeleton of mouthpad 32 to conform mouthpad 32 to a desired shape. Stiffening member 11 may be formed of wire or other suitable material. When a user bites down on mouthpad 32, the upper teeth and the lower teeth compress the air inside air pocket 9. As a result, the air pressure forces the resilient material of mouthpad 32 to conform to the shape of the users teeth, forming balloons which block the irregular spaces formed by, for example, misaligned or missing teeth.

Figure 4:
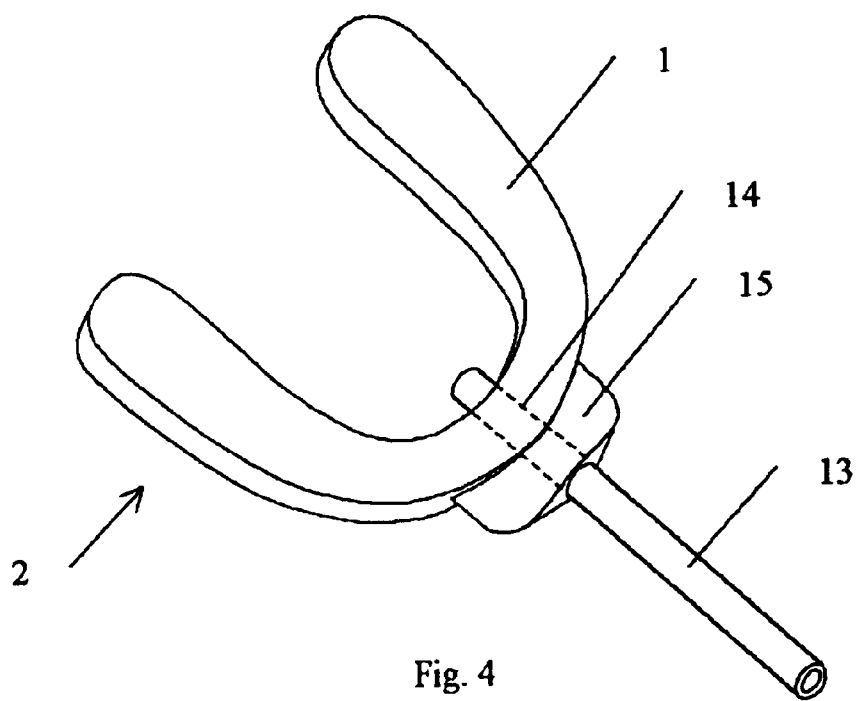
FIG. 4 is a schematic perspective view of another alternative embodiment of the teeth crevice cleaning apparatus of FIG. 1, shown with a suction tube.

In certain preferred embodiments, a suction tube 13 can be attached to plate 1 of mouthpad 2, as seen in FIG. 4. Suction tube 13 extends through the forward portion of plate 1 at the base of the U-shape, that is, the portion which is between the front teeth of the user. Tube 13 provides a channel to bring liquid, such as mouthwash, into the mouth from a container (not shown). A user can then advantageously insert and properly align mouthpad 2 before placing liquid in their mouth. The section 14 of tube 13 which is within plate 1 is preferably formed of an elastic material. Therefore, when compressed by the jaw, section 14 is compressed and closed off to stop liquid flow through tube 13. A shoulder 15 may be attached to the front of plate 1, having tube 13 extending therethrough. Shoulder 15 may be formed of the same material as plate 1, or any other suitable material. Shoulder 15 is shaped to provide a smooth interface with the lips of a user to prevent leakage.

In certain preferred embodiments, the mouthpad can be coated with or otherwise contain an antiseptic substance and/or other substance such as flavoring. For example, the mouthpad can be soaked with an antiseptic liquid, such as mouthwash.

In another preferred embodiment, the mouthpad is formed of chewing gum material. Conventional chewing gum can easily be formed into the desired U-shaped mouthpad. The plasticity of the gum provides the function of blocking the spaces between the upper teeth and the lower teeth. The mouthpad can then be chewed in conventional manner after it is used to clean teeth.

Figure 5:
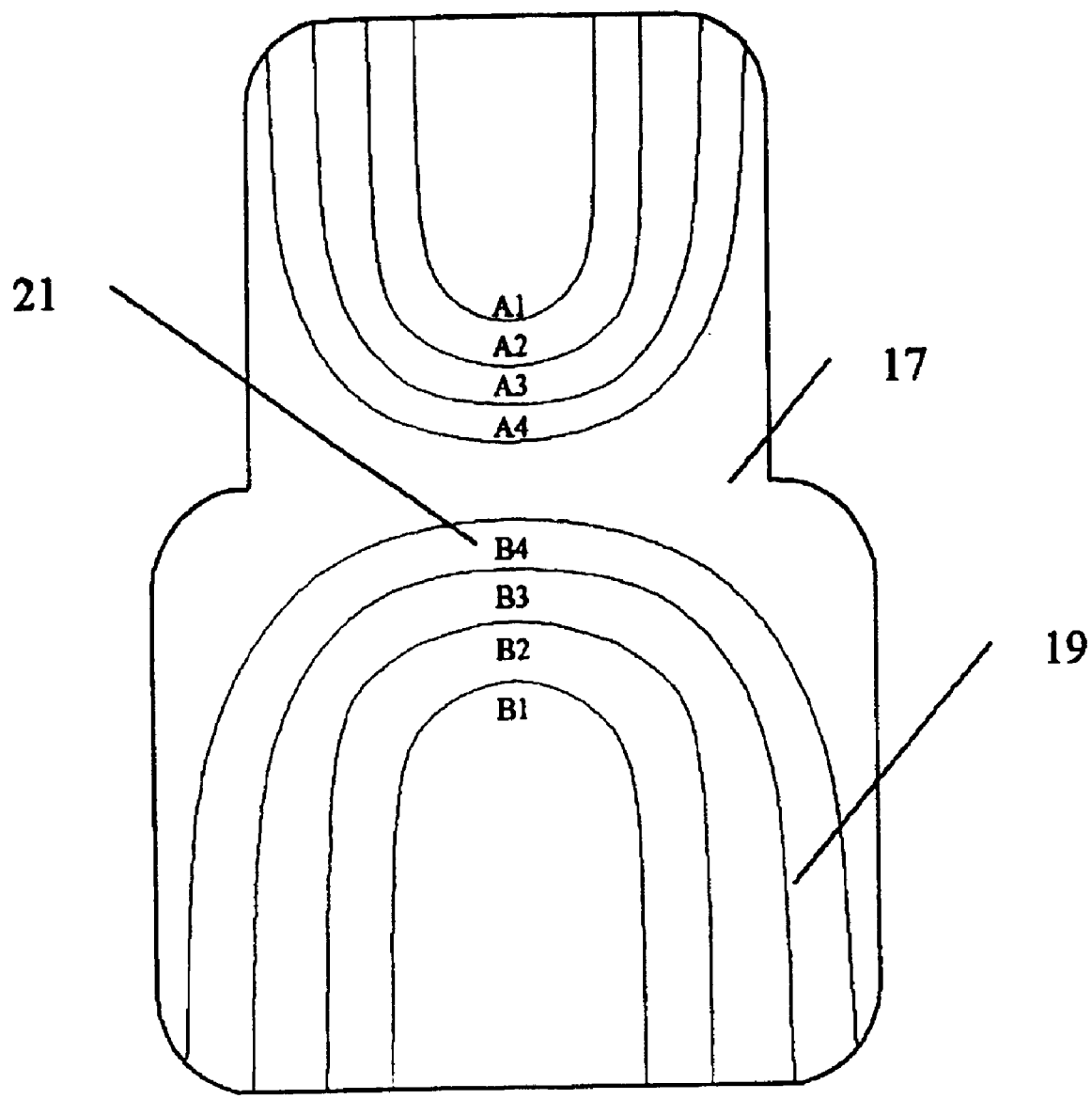
FIG. 5 is a schematic plan view of a measurement card suitable for use in conjunction with the teeth crevice cleaning apparatus of FIG. 1.

To fit different jaw sizes, different sized mouthpads are needed. As seen in FIG. 5, a measurement card 17 is designed for selecting a suitable sized mouthpad. Such cards are disposable and made of a sheet of soft material easily accepting teeth marks. Suitable materials include, for example, cardboard, plastic, and Styrofoam. Measurement card 17 is marked with size indicating lines 19 which are labeled by size marks 21 which reference the different sizes for mouthpads. In a preferred embodiment, a booklet of measurement cards 17 is made available next to the mouthpads in a store for a customer to use in selecting a suitably sized mouthpad.

In another preferred embodiment, the mouthpad may be formed of gelatin-like material with a self-hardening function. A piece of such material is put into the individual's mouth and positioned between the upper and lower teeth covering the biting surfaces of the teeth. The individual then bites down on the piece of material for a certain amount of time to form a customized jaw shaped pad, which has the individual's teeth prints embedded in it. After being removed from the mouth, the stiffened pad can be modified, if necessary, into a mouthpad, or can be made into a mouthpad according to the shape of the jaw. Thus, such a mouthpad is customized to the individual's teeth contour and jaw size.

A kit according to the present invention comprises plate 1 and a liquid for rinsing the teeth crevices. The liquid may be, for example, mouthwash specifically designed for rinsing teeth. Plate 1 of the kit may, in certain preferred embodiments, include tube 13 and shoulder 15, and/or handle 7.

When using the teeth crevice cleaning apparatus, a user first puts the mouthpad into their mouth and then draws mouthwash or other liquid into the mouth. Alternatively, the mouthwash or other liquid may be drawn into the mouth before the mouthpad is inserted into the mouth. In certain preferred embodiments, the mouthwash can be drawn into the mouth with a suction tube. After an appropriate amount of mouthwash enters the mouth, the user bites down on the mouthpad to block the spaces between the upper teeth and the lower teeth. In embodiments using a suction tube, biting down on the mouthpad also closes off the suction tube. The user then rinses in conventional manner, by pushing the mouthwash from the oral cavity, that is, between the rear of the teeth and the pharynx, to the buccal cavity, that is, between the lips and cheeks and the front of the teeth and then, vice versa. Since the mouthpad is substantially blocking the larger spaces between the upper teeth and the lower teeth, most of the mouthwash is forced to flow though the crevices between the teeth. This generates great shear forces that detach and wash away residues that adhere to the hard-to-reach surfaces, thus cleaning the crevices between teeth. When rinsing, the occluded teeth act as a filter and catch anything too large to pass through the crevices between teeth. To remove the caught residues, mouthwash may be spat out on each side of the teeth respectively. After rinsing for a sufficient time, the user spits out the mouthwash from one side of the teeth. Additional mouthwash may then be drawn into the mouth for a second rinsing, after which the user spits out the mouthwash from the other side of the teeth. The mouthpad is then removed from the mouth. In embodiments where the mouthpad is formed of chewing gum, the mouthpad is chewed rather than removed from the mouth.

To select a suitable mouthpad, a user places a measurement card in their mouth and bites down on the card to make teeth marks. After taking the card out of their mouth, the user can compare the location of teeth marks to the size lines on the card to determine the appropriate size mouthpad for that user's teeth.

In light of the foregoing disclosure of the invention and description of the preferred embodiments, those skilled in this area of technology will readily understand that various modifications and adaptations can be made without departing from the true scope and spirit of the invention. All such modifications and adaptations are intended to be covered by the following claims.

We claim:

1. A method of cleaning teeth comprising the following steps, in combination:

inserting a U-shaped plate sized to cover substantially only the biting surfaces of upper and lower teeth of a human jaw into a mouth of a user;

drawing an appropriate amount of liquid into the mouth;

biting down on the plate;

rinsing the liquid repeatedly while biting down on the plate;

spitting out the liquid; and removing the plate from the mouth.

2. The method according to claim 1, wherein the liquid is drawn into the mouth through a tube extending through the plate.

3. The method according to claim 1, wherein the plate is formed of resilient material.

4. A method of cleaning crevices between adjacent teeth of a human jaw, the method comprising inserting a plate between upper teeth and lower teeth of the jaw of a user, drawing a liquid into a mouth of the user, biting down on the plate to cover substantially only the biting surfaces of the upper teeth and the lower teeth and to substantially block spaces between the upper teeth and the lower teeth, and forcing the liquid through the crevices between adjacent teeth of the upper jaw and adjacent teeth of the lower jaw while the biting surfaces remain substantially covered by the plate.

* * * * *

UNITED STATES PATENT AND TRADEMARK OFFICE
CERTIFICATE OF CORRECTION

PATENT NO.    : 6,439,889 B1
DATED         : August 27, 2002
INVENTOR(S)   : Chen et al.

It is certified that error appears in the above-identified patent and that said Letters Patent is hereby corrected as shown below:

<u>Title page,</u>
Item [75], Inventors, "Linguin Chen" should read -- Lingjun Chen --.

Signed and Sealed this

Twenty-eighth Day of January, 2003

JAMES E. ROGAN
*Director of the United States Patent and Trademark Office*